US006626569B2

(12) United States Patent
Reinstein et al.

(10) Patent No.: US 6,626,569 B2
(45) Date of Patent: Sep. 30, 2003

(54) QUALITY ASSURANCE SYSTEM FOR A MEDICAL LINEAR ACCELERATOR

(75) Inventors: Lawrence E. Reinstein, Port Jefferson, NY (US); Keith Welsh, Sound Beach, NY (US)

(73) Assignee: The Research Foundation of Suny, Stony Brook, NY (US)

( * ) Notice: Subject to any disclaimer, the term of this patent is extended or adjusted under 35 U.S.C. 154(b) by 0 days.

(21) Appl. No.: 09/870,094

(22) Filed: May 30, 2001

(65) Prior Publication Data

US 2002/0181660 A1 Dec. 5, 2002

(51) Int. Cl.$^7$ .................. G01D 18/00; G21K 5/00; H05H 9/00
(52) U.S. Cl. .................. 378/206; 378/64; 378/206; 378/207; 250/252.1; 315/505
(58) Field of Search .................. 378/65, 162, 163, 378/164, 165, 166, 207, 205, 206, 64; 315/505; 250/252.1

(56) References Cited

U.S. PATENT DOCUMENTS

| | | | | |
|---|---|---|---|---|
| 3,971,470 A | * | 7/1976 | White | 206/455 |
| 4,400,827 A | * | 8/1983 | Spears | 378/207 |
| 5,052,035 A | * | 9/1991 | Krupnick | 378/163 |
| 5,511,107 A | * | 4/1996 | Sliski | 378/207 |
| 5,544,238 A | * | 8/1996 | Galkin | 378/207 |
| 5,565,678 A | * | 10/1996 | Manian | 250/252.1 |
| 5,684,854 A | * | 11/1997 | Hughes | 378/206 |
| 5,754,622 A | * | 5/1998 | Hughes | 378/65 |
| 6,052,430 A | * | 4/2000 | Siochi et al. | 378/65 |
| 6,125,335 A | * | 9/2000 | Simon et al. | 702/85 |
| 6,260,999 B1 | * | 7/2001 | Wofford et al. | 378/205 |
| 6,364,529 B1 | * | 4/2002 | Dawson | 378/207 |
| 6,409,383 B1 | * | 6/2002 | Wang et al. | 378/207 |

* cited by examiner

Primary Examiner—Drew A. Dunn
Assistant Examiner—Allen C. Ho
(74) Attorney, Agent, or Firm—Dilworth & Barrese, LLP

(57) ABSTRACT

An image-based quality assurance (IBQA) system is provided for performing quality assurance testing of a medical linear accelerator photon beam. The IBQA system includes an imaging phantom integrated with an automated image analysis system. The imaging phantom comprises a set of fixed and rotatable reference objects which, when radiographed, set the orientation of the phantom, determine magnification factors and measure spatial distortions. The imaging phantom includes a chamber for inserting a radiographic film to record an image of the photon beam. The sampled image is digitized and made available to the automated image analysis system for measuring quality assurance parameters from the sampled image. The measured beam quality parameters are compared with baseline parameter values to determine whether they fall within prescribed specifications. The analysis system includes an integrated database which stores the measured parameters to: establish baseline and tolerance tables for all measured image quality assurance parameters for each accelerator modality and energy; record and retrieve beam quality parameter results for trend analysis and data mining for most AAPM TG-40 beam parameters; select specific protocols for defining the image quality assurance parameters; and generate customized reports responsive to government mandated regulations.

15 Claims, 10 Drawing Sheets

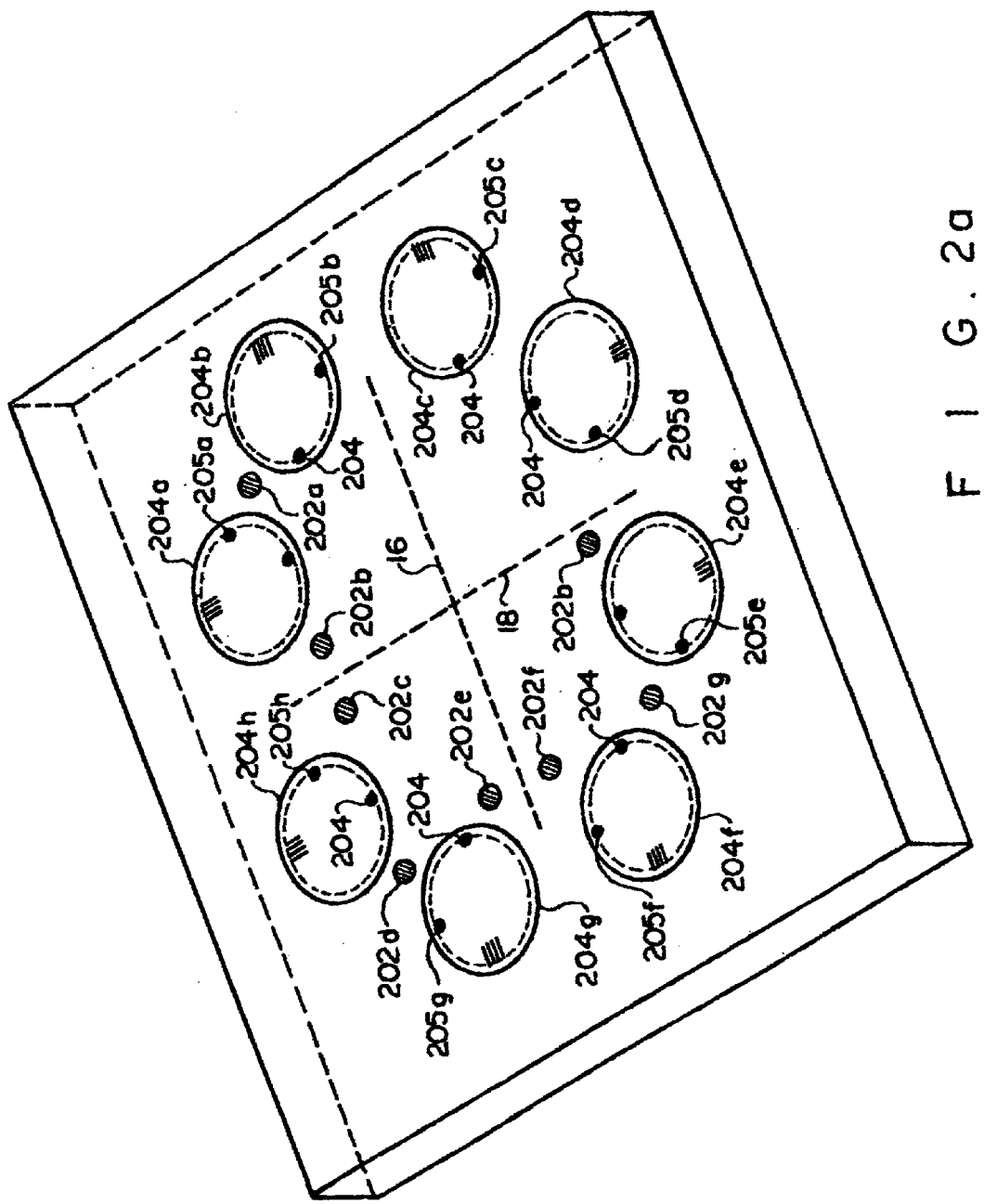

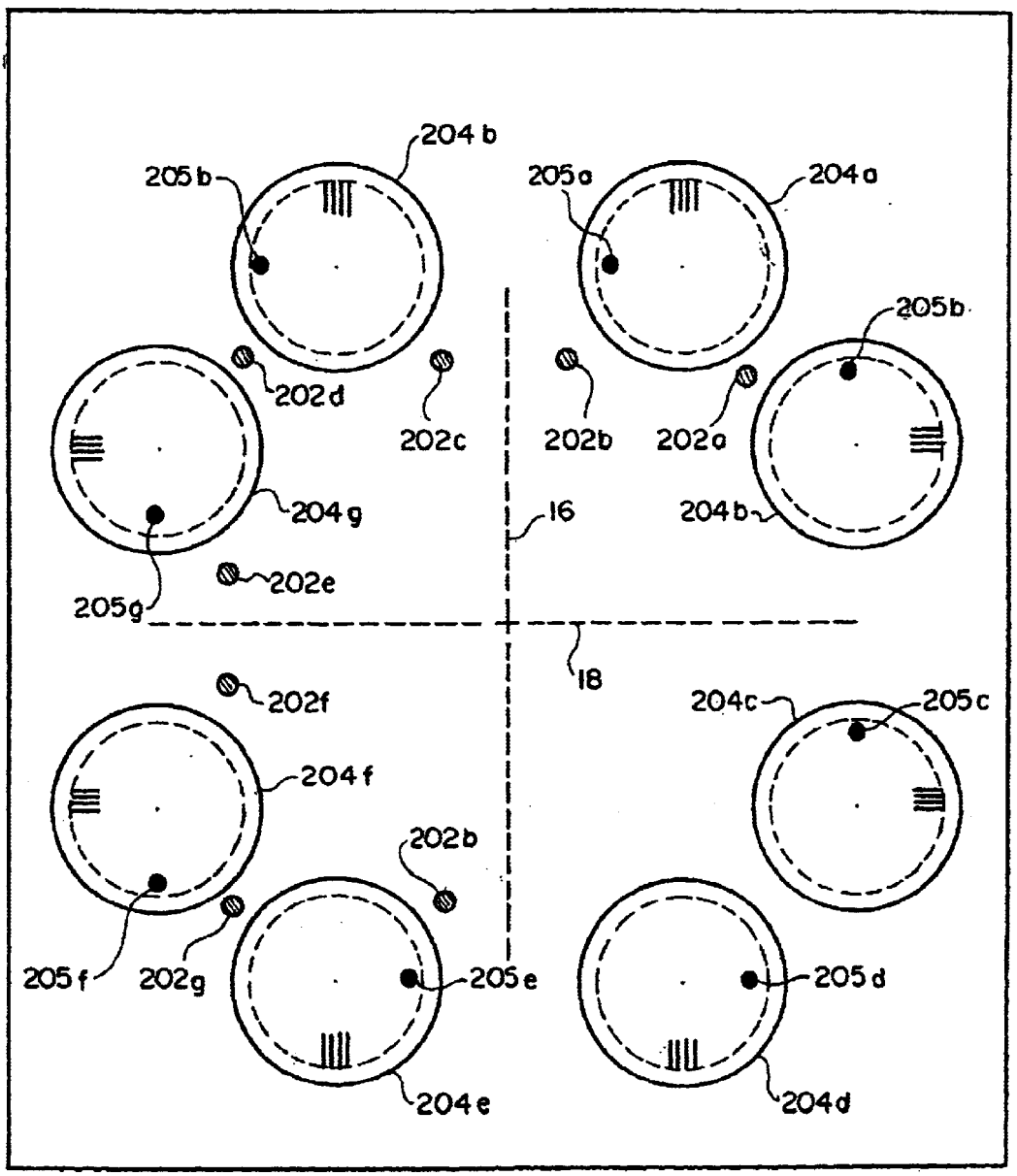
F I G. 2b
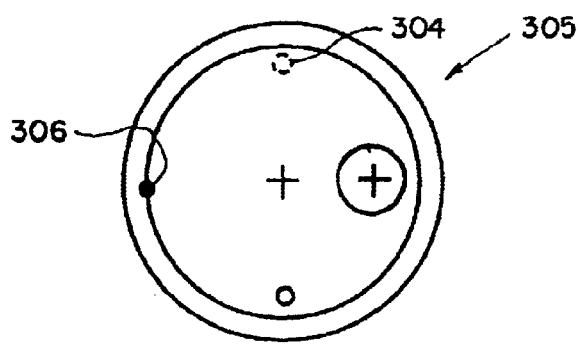
F I G. 3

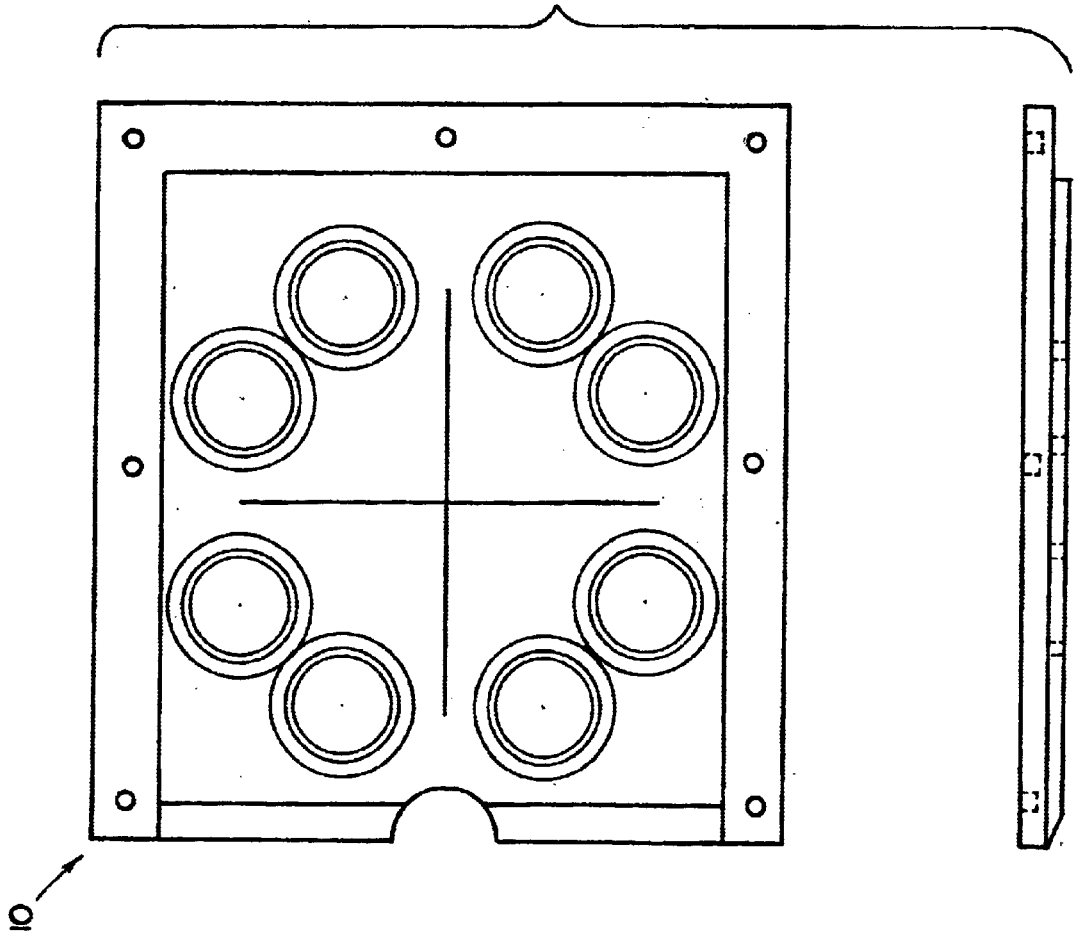

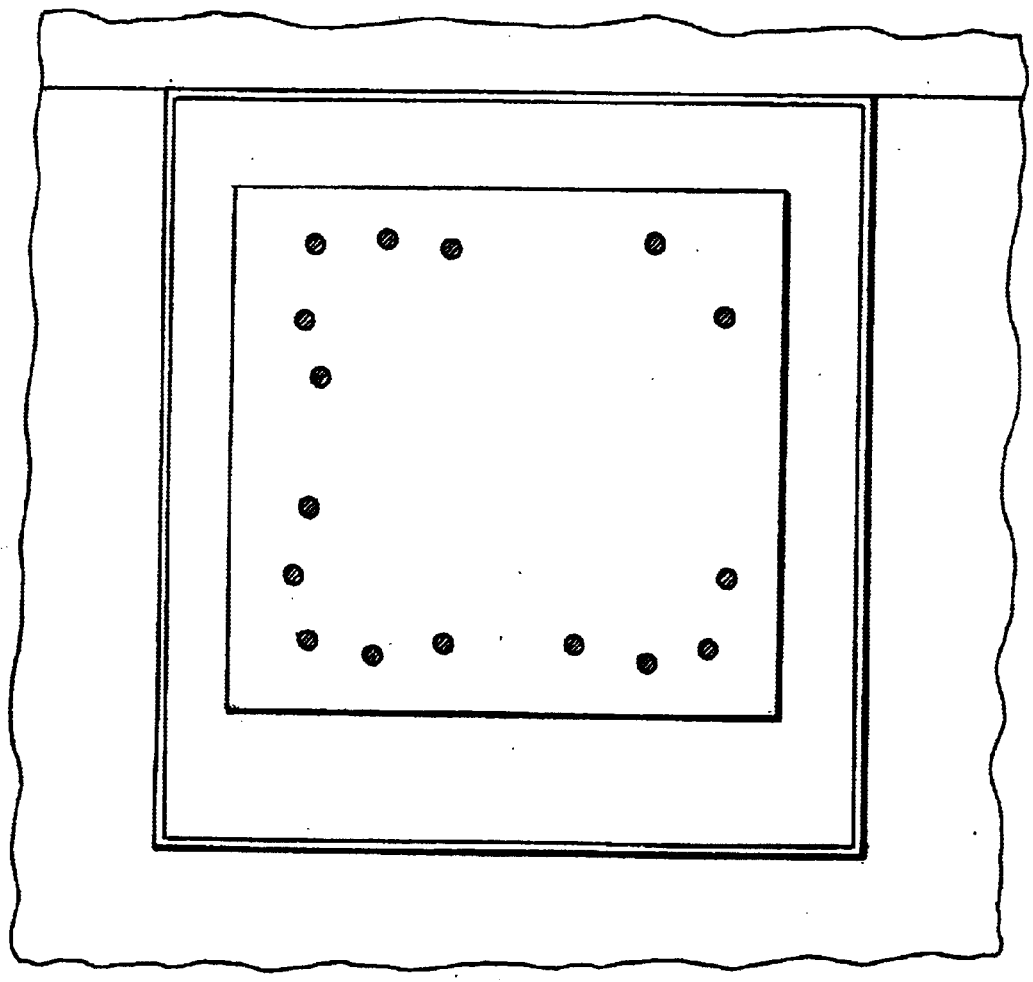
F I G. 4

FIG. 6

QA WIZARD REPORT

RADIATION FLATNESS (%)

| | |
|---|---|
| Tolerance | 3.0 |
| Baseline Longitudinal | 2.0 |
| Baseline Transverce | 2.0 |
| Longitudinal | 1.9 |
| Transverce | -1.0 |

RADIATION SYMMETRY (%)

| | |
|---|---|
| Tolerance | 3.0 |
| Baseline Longitudinal | 2.0 |
| Baseline Transverce | 2.0 |
| Longitudinal | 3.7 |
| Transverce | 2.1 |

CROSS-HAIR DISPLACEMENT (mm)

| | |
|---|---|
| Tolerance | 2.0 |
| Baseline Longitudinal | 0.0 |
| Baseline Transverce | 0.0 |
| Longitudinal | -0.7 |
| Transverce | -0.6 |

RADIATION FIELD SIZE (mm)

| | |
|---|---|
| Tolerance | 2.0 |
| Baseline Longitudinal | 200.0 |
| Baseline Transverce | 200.0 |
| Longitudinal | 199.6 |
| Transverce | 197.8* |

RADIATION EDGE ANGLE (deg)

| | |
|---|---|
| Tolerance | 1.0 |
| Baseline Longitudinal | 0.0 |
| Baseline Transverce | 0.0 |
| Superior | -0.4 |
| Inferior | -0.5 |
| Left | -0.6 |
| Right | -0.5 |

RADIATION FIELD PENUMBRA (mm)

| | |
|---|---|
| Tolerance | 2.0 |
| Baseline Longitudinal | 5.0 |
| Baseline Transverce | 5.0 |
| Superior | 4.7 |
| Inferior | 4.7 |
| Left | 4.1 |
| Right | 4.1 |

LIGHT / RADIATION FIELD EDGE COINCIDENCE (mm)

| | |
|---|---|
| Tolerance | 1.0 |
| Baseline Longitudinal | 0.0 |
| Baseline Transverce | 0.0 |
| Superior | -0.5 |
| Inferior | 0.2 |
| Left | -0.4 |
| Right | -0.3 |

LIGHT FIELD SIZE (mm)

| | |
|---|---|
| Tolerance | 2.0 |
| Baseline Longitudinal | 200.0 |
| Baseline Transverce | 200.0 |
| Longitudinal | 199.9 |
| Transverce | 198.5 |

LIGHT FIELD CENTER DISPLACEMENT (mm)

| | |
|---|---|
| Tolerance | 1.0 |
| Baseline Longitudinal | 0.0 |
| Baseline Transverce | 0.0 |
| Longitudinal | -0.4 |
| Transverce | 0.1 |

*: Needs Attention

FIG. 7

QUALITY ASSURANCE SYSTEM FOR A MEDICAL LINEAR ACCELERATOR

BACKGROUND OF THE INVENTION

1. Field of the Invention

The present invention relates to a medical linear accelerator (LINAC). More particularly, the present invention relates to a radiation treatment beam quality assurance system for monitoring and assessing quality assurance parameters of a radiation treatment beam for a medical LINAC using image analysis methods.

2. Description of the Related Art

Medical accelerator based radiotherapy using a medical linear accelerator (LINAC) is a potentially curative treatment modality for a variety of cancers. Its effectiveness, however, is highly dependent on the radiation dose being delivered. The current standard of dose accuracy is better than +/−5% with a geometric precision of 1 mm–5 mm, depending on the treatment site. In order to guarantee such a demanding accuracy, performance guidelines for medical LINAC beams have been established by governmental organizations, as well as professional organizations, such as the American Association of Physicists in Medicine (AAPM) Task Group-40 (TG-40). TG-40 recommends that a radiation oncology physicist perform monthly measurements of the following LINAC beam image quality assurance parameters: radiation beam symmetry, radiation beam uniformity, digital readouts of radiation field size, coincidence between the light beam localizer and the radiation field, accuracy of beam cross-hair placement, constancy of radiation field penumbra, collimator jaw angle and alignment.

Using traditional methods, such measurements are both difficult to make and time consuming. Moreover, making such measurements represents only a small portion of the overall burden of quality assurance testing. Analyzing, evaluating, and tracking the measured data represent additional burdens on the system.

Accordingly, there is a need for an improved image quality assurance system that is fast and efficient. There is also a need for a system that is capable of capturing more data with higher spatial resolution than with conventional point or linear scanner measurement techniques. There is also a corresponding need for a way to analyze, evaluate, and track the measured data.

SUMMARY OF THE INVENTION

The present invention provides an integrated measurement and analysis system, referred to herein as an image-based quality assurance (IBQA) system for providing automated quality assurance testing of a medical linear accelerator (LINAC) used in therapeutic radiation treatment. Instead of using conventional methods of beam quality verification which are error prone and time consuming, the IBQA system according to the present invention provides an efficient and robust method of quality assurance testing that is fast, reliable and objective.

In accordance with one aspect of the present invention, the IBQA system includes two parts, an imaging phantom and an integrated image analysis (IIA) system. The imaging phantom is preferably made of an opaque polystyrene composite made of two substantially square opaque plastic plates mated together by fastening screws. A middle region of the top plate is bored out to a few millimeters in depth such that when the two plates are mated to one another a chamber or slot is formed therein for receiving radiographic film.

In operation, the imaging phantom is exposed to a beam of radiation which is recorded on the radiographic film. In an alternate embodiment, an electronic portal imaging device may be used to record the beam of radiation.

The imaging phantom further includes a set of fixed reference markers, which are radio-opaque, embedded substantially flush within the top plate of the imaging phantom. The fixed markers are positioned adjacent to the chamber or slot which, when radiographed, set the orientation of the phantom, determine x-y scaling factors and measure spatial distortions. Establishing x-y scaling factors is required to correct for distortions which occur when the sampled LINAC beam image is digitized in a film scanner prior to performing an analysis. It is well known that a digitizing operation can distort scaling differently in the x and y directions. Therefore, some means of correcting for this distortion is required. The fixed disk markers serve to correct for this distortion.

The imaging phantom further includes eight rotatable radio-opaque markers for determining the degree of misalignment between the radiation field edges and a localizing light field of the LINAC.

The IIA system is configured to operate with the imaging phantom and includes hardware and software for analyzing, storing, and tracking a plurality of LINAC beam image quality assurance parameters from a sampled LINAC beam image. The software used in the IIA system is specifically tailored to the imaging phantom allowing an operator to load an image, register and analyze that image by simply clicking the mouse button twice on an IIA display screen.

The IIA system includes viewing and processing software for evaluating the sampled beam image; display means to display the measured beam image quality assurance parameters to allow comparison with baseline beam quality assurance parameters to determine whether one or more parameters are outside a prescribed threshold; and software for producing quantitative reports in accordance with government mandated regulations (e.g., American Association of Physicists in Medicine TG-40 guidelines); an integrated database which stores the measured parameters to: establish baseline and tolerance tables for all beam image quality assurance parameters for each accelerator modality and energy; record and retrieve beam quality parameter results for trend analysis and data mining for most AAPM TG-40 beam quality assurance parameters; select specific protocols, such as from "Protocol and procedure for quality assurance of linear accelerators" by Chris Constantinou, for defining the beam image quality assurance parameters; and generate customized reports responsive to government mandated regulations.

A method consistent with the present invention for employing the inventive IBQA system includes the steps of: setting up the imaging phantom including the steps of: leveling the imaging phantom; aligning light field cross hairs of a LINAC with cross hairs on the imaging phantom; and aligning marks on rotatable disks with a light field edge of the LINAC's light localizer. Subsequent to setting up the imaging phantom, exposing a sheet of radiation sensitive film contained within the imaging phantom to a beam of energy to obtain a sampled image; digitizing the sampled image; detecting the radiation field edges in the sampled image; searching the sampled digitized image for the image of a plurality of fixed and rotatable radio-opaque disk markers; measuring a plurality of beam quality assurance parameters from the sampled image; displaying the measured beam quality assurance parameters along with a set of baseline beam quality assurance parameters highlighting those measured beam quality assurance parameters which fall outside an acceptable range as defined by a corresponding baseline beam quality parameter; and storing the measured beam quality assurance parameters in a database for providing customized reports and for tracking the parameters over time.

The IBQA system disclosed will have great value to test operators and other agents responsible for analyzing and reporting quality test results of a medical LINAC. The time required to make beam image quality measurements is significantly reduced while providing greater accuracy an higher reliability than conventional techniques of radiation beam measurement and quality testing.

BRIEF DESCRIPTION OF THE DRAWINGS

The foregoing features of the present invention will become more readily apparent and may be understood by referring to the following detailed description of an illustrative embodiment of the present invention, taken in conjunction with the accompanying drawings, where:

FIG. 2a is a perspective view of an imaging phantom according to the present invention;

FIG. 2b is a top view illustration of an imaging phantom according to the present invention;

FIGS. 2c, 2d are top views of mechanical illustrations of an imaging phantom according to the present invention;

FIG. 3 is an illustration of a rotating disk with embedded radio-opaque marker of the imaging phantom of FIG. 2;

FIG. 4 is an illustration of an exposed sheet of radiographic film showing the recorded radiation field including images of the radio-opaque markers;

Figure 6:
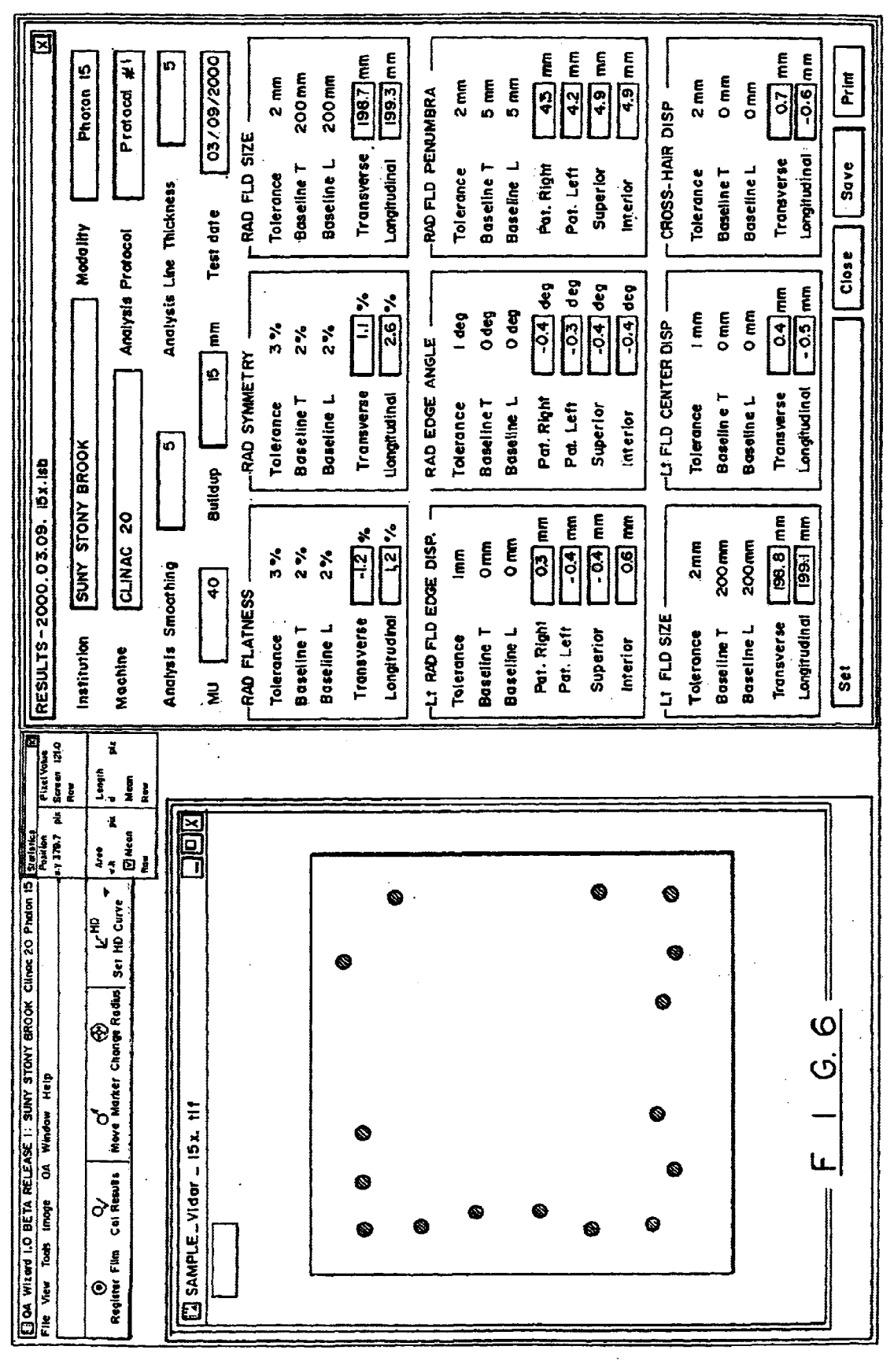

FIG. 6 is a screen shot of a display of the IBQA system according to the present invention;

FIG. 7 is an exemplary report generated by the report generation module of the image-based quality assurance (IBQA) system.

DETAILED DESCRIPTION OF THE PREFERRED EMBODIMENTS

The following detailed description is of the best mode presently contemplated for carrying out the invention. This description is not to be taken in a limiting sense, but is made merely for the purpose of describing the general principles of the invention. The scope of the invention should be determined with reference to the claims.

A. System Overview

Figure 1:
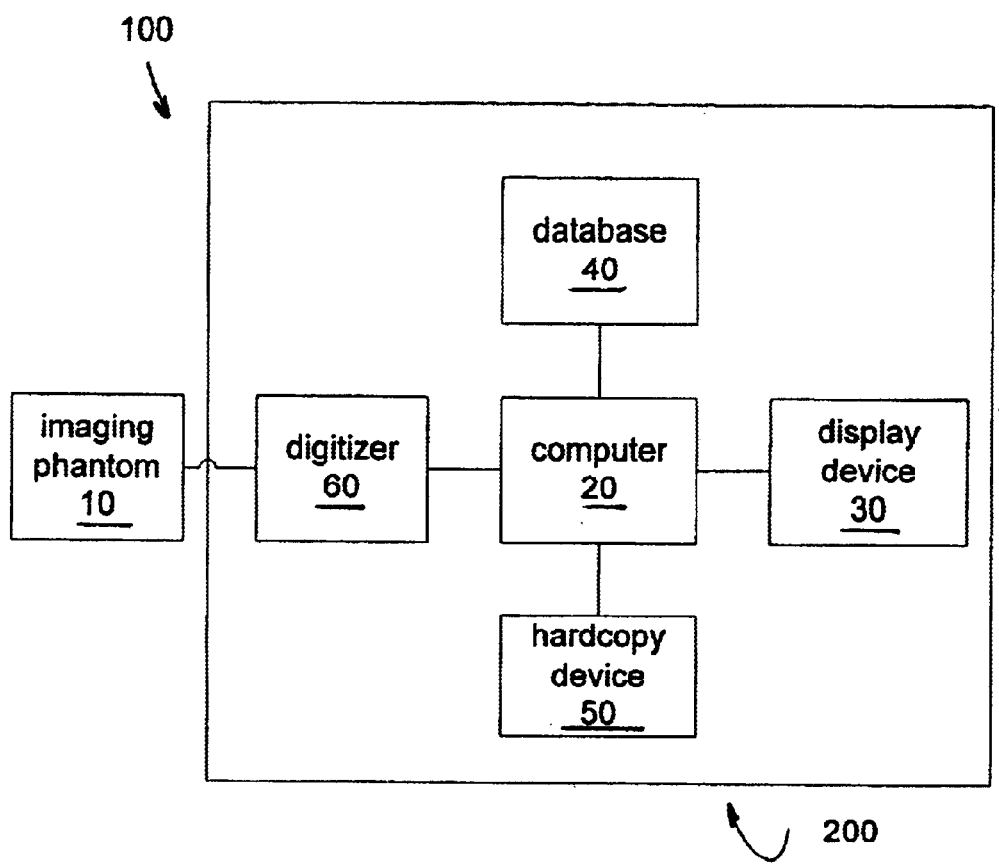
FIG. 1 is a block diagram of an image-based quality assurance (IBQA) system according to the present invention.

An illustrative imaged-based quality assurance system 100 of the invention is illustrated FIG. 1. The system 100 includes an imaging phantom 10 connected to an integrated image analysis (IIA) system 200 which includes a general purpose computer 20, which may be embodied as any general purpose PC having at least a Pentium 90™ processor, or equivalent thereof, at least 32 MB of RAM, and at least 16K colors. The general purpose computer may be, for example, an IBM-PC™ compatible or Apple Macintosh™ computer. In the presently preferred embodiment, the general purpose computer 20 operates under the WINDOWS 95™ operating system by Microsoft™. Other operating systems under which the general purpose computer 20 may run under include Windows 98™, Windows NT™ and Windows 2000™.

The system software is written in Visual Basic™ and in C++™, using structured programming techniques. The system software includes software methods for computing beam quality assurance parameters; analyzing the measured parameters to determine whether they fall within prescribed limits; and for manually analyzing a sampled image.

The IIA system 200 also includes an image display device 30 which may be some type of high color resolution CRT device (e.g., at least 16k colors); a database 40 which is typically a mass storage device, such as disk storage; an image hard copy device 50 which would typically be a laser printer for paper copies of the images; and a digitizer for digitizing a beam sample on radiographic film. Hard copy device 50 and digitizer 60 exchange signals with the general purpose computer 20 on a general-purpose interface, such as an asynchronous port (i.e., using the RS-232C protocol of the PC unit). In one embodiment, the IIA system 200 includes an electronic portable imaging device (EPID) (not shown) to record a digital image of a photon beam directly, as an alternative to using radiographic film.

Database 40 is preferably part of, or otherwise connected to the general purpose computer 20. In the preferred embodiment the database 40 is implemented using the file formats used in Microsoft Access™ to allow the database 40 to be viewed in Microsoft Access™. The database 40 is used to store information relating to the LINACS and the institutions in which they are located. Generally, the database 40 stores the following: a list of LINACS the operator is responsible for. This list is created during an initial program configuration; the beam modalities of the listed LINACS; the analysis protocols, including baseline and tolerance values, for calculating the LINAC treatment beam quality assurance (QA) parameters; other analysis preferences (not associated with any protocol); and analysis results including the calculated QA parameters as well as protocol, baseline and tolerance values, other preferences, dates, and other information used at the time of performing film (image) analysis.

Figure 2D:
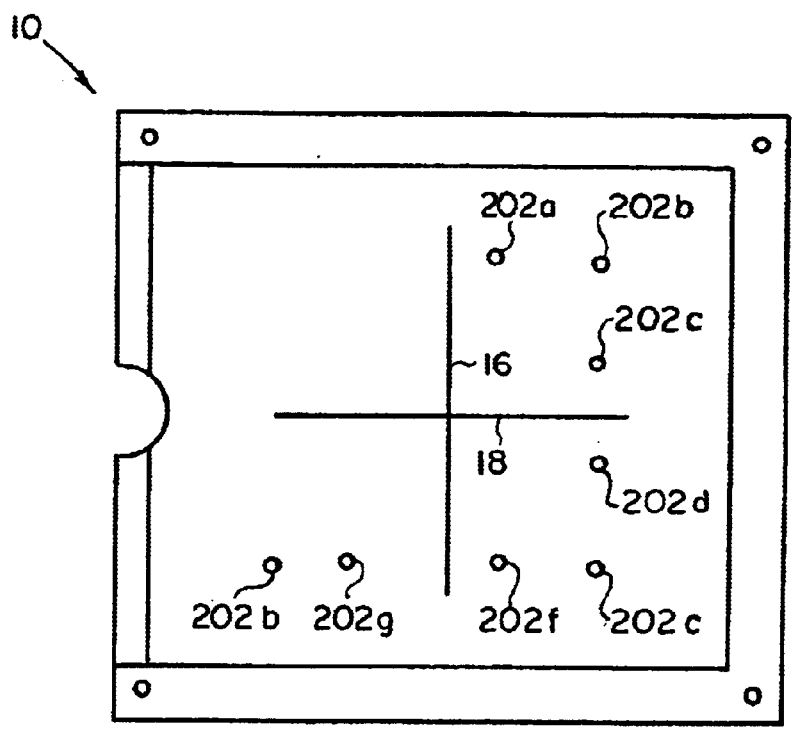
Figure 2E:
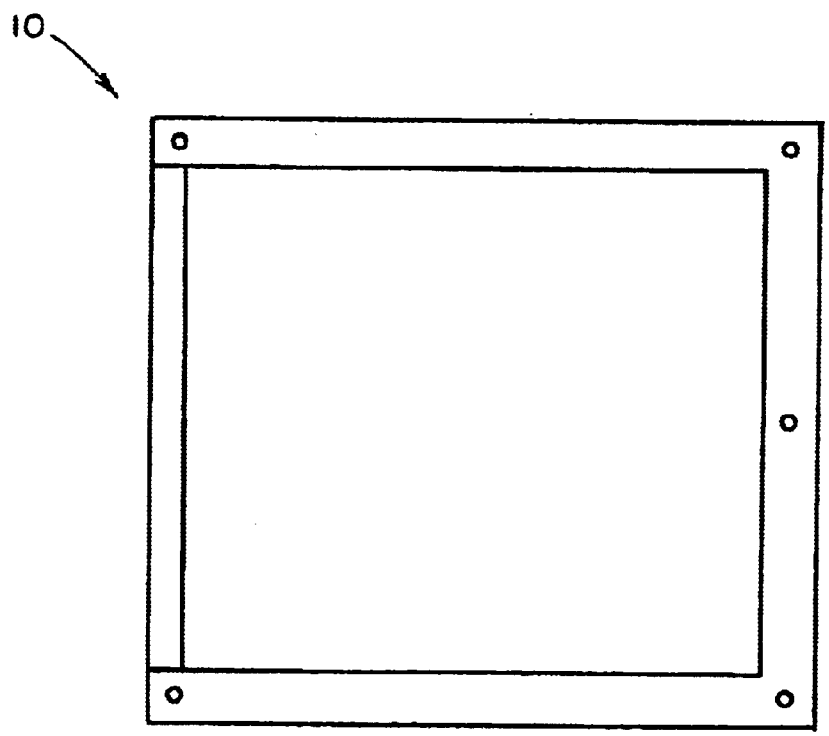
FIG. 2e is a view of the bottom plate of the imaging phantom of FIG. 2.

Mechanical aspects of the imaging phantom 10 are illustrated in FIG. 2. The imaging phantom 10 is, in one embodiment, a 25×30×3 $cm^3$ polystyrene composite including two substantially square opaque plastic plates, a top plate, as shown in FIGS. 2a through 2d, and a bottom plate, as shown in FIG. 2e. The top and bottom plates are mated together by fastening means, such as screws, as shown in FIG. 2c through 2e. The top surface of the imaging phantom 10 is manufactured substantially flat to allow for the placement of additional buildup material for use with higher energy beams. Prior to mating the top and bottom plates together, a middle region of the top plate is bored out to a few millimeters in depth such that when the two plates are mated to one another a chamber or slot is formed therein. The chamber or slot forms a receptacle positioned 1.5 cm below the top surface of the phantom for receiving a 10"×12" sheet of radiographic film, such as Kodak™ XV-2 film. The film is preferably contained within a light sealed paper envelope to prevent inadvertent exposure prior to being irradiated by the LINAC beam. One and one-half centimeters of polystyrene lies below the slot for backscatter.

FIG. 2a is a perspective view of the imaging phantom 10 illustrating two scribed cross hair lines 16, 18 visible on the top surface of the phantom used for alignment with cross hairs of the LINAC. The cross hair lines 16, 18 are referenced to the fixed markers 202a–h within the imaging phantom 10 and thus correlate the radiation machine cross hair coordinate system with the imaging phantom 10 coordinate system. Also shown in FIG. 2a are sixteen tungsten radio-opaque markers, embedded in the top plate 202a–h, 205a–h (to be described).

FIG. 2b is a top view of the top plate which illustrates the sixteen tungsten radio-opaque markers, embedded in the top plate. Eight of the embedded markers 202a–h are fixed at precise positions within the imaging phantom 10. While tungsten is a preferred material, theoretically a number of different materials could be used for the markers including for example, steel, titanium, lead. In general, most metals are candidates for use, however, heavier metals are preferred for their higher atomic number. Tungsten is a preferred material because of its high atomic number leading to more absorption of radiation and therefore a higher quality image. The eight fixed markers 202a–h are positioned linearly along each of the two orthogonal directions with the eighth marker positioned to destroy the symmetry of the layout to enable the determination of the alignment of the LINAC gantry in the case where the imaging phantom is set up correctly. Without the eighth marker, multiple orientations of the film with respect to the LINAC could occur with each orientation producing the exact same image with respect to the positioning of the fixed markers. The eight fixed tungsten markers 202a–h, as labeled in FIG. 2a, 2b and 2d, are used to establish a reference coordinate system, determine x and y magnification factors and measure spatial distortions, as further described below.

FIG. 2b further shows eight rotatable tungsten disk markers 205a–h, which are embedded in 8 rotatable wheels 204a–h situated around the edge of a 20×20 cm field region of the imaging phantom 10. The rotatable disk markers 205a–h within the wheels 204a–h are situated 90 degrees from a tiny black dot 207 on the surface of each disk and are used to localize the light field emitted from the LINAC radiation machine.

FIGS. 2c and 2d are top views which illustrate mechanical aspects of eight rotatable tungsten disk markers 205a–h of the imaging phantom 10.

FIG. 2e illustrates mechanical aspects of the bottom plate of the imaging phantom.

B. System Operation

The process by which the IBQA system acquires a sampled image to determine beam quality assurance parameters will now be described.

B.1 Image Acquisition

Image acquisition generally includes the steps of: setting up the imaging phantom; exposing the film to a beam of energy; detecting the radiation field edges in the sampled image; searching for a number of markers in the sampled image to establish an x-y coordinate system and to determine the light field position; and measuring the image quality assurance parameters. Each of the above steps are described in detail below;

In operation, image acquisition starts by setting up the imaging phantom 10. The steps for setting up the imaging phantom 10 according to one embodiment include: positioning the imaging phantom on top of a tripod to ensure a stable, level platform. It is contemplated that the imaging phantom 10 may also include leveling feet to allow for placement of the phantom directly on top of a treatment couch in lieu of a tripod. Irrespective of how the imaging phantom 10 is supported, the phantom 10 is positioned with a SSD of 100 cm from the LINAC emitter, where the acronym SSD refers to the source of radiation to surface of patient or phantom distance.

After the imaging phantom 10 is properly positioned at an appropriate distance from the LINAC emitter, a sheet of radiographic film is inserted into the imaging phantom 10. In an alternate embodiment, an electronic portal imaging device (EPID) device may substitute for the radiographic film. In the case where an EPID device is used, the information from the transmission of the radiation through the phantom is recorded below the treatment couch at the EPID's level. Next, the imaging phantom 10 cross-hairs 16, 18 are aligned with the LINAC light localizer cross hairs which project from the emitter. Once the operator has established an alignment between the imaging phantom cross hairs 16, 18 and the LINAC light localizer cross hairs, the imaging phantom is considered to be centered.

The LINAC field size is then adjusted to 20×20 $cm^2$, as verified by a direct read out on a LINAC display. While, the preceding steps insure alignment between LINAC light localizer cross hairs and the imaging phantom cross hairs 16, 18 it cannot be assumed that the photon beam emission will project exactly where the light beam projects on the surface of the imaging phantom 10. TG 40 suggested tolerance between the projection of the radiation and light beam is on the order of +/−2 mm. The phantom can only measure light field edges that are within +/−1 cm from edge of the 20×20 field size as defined by the phantom. The rotatable disk markers 205a–h serve to quantify the difference between the edges of the projection of the light beam and the edges of the projection of the photon beam to insure that the measured differences are within tolerance. Because it is not possible to pass the LINAC's light beam through the top of the imaging phantom 10 onto the film, the rotating disk markers 205a–h provide information about the position of the edge of the light field by indirect means, as described below with reference to FIG. 3.

FIG. 3 is an illustration of one of the rotating markers 304 shown embedded within a rotating wheel 305. The rotating disk 304 represents one of the key innovative concepts of the present invention. The use of a rotating disk, as opposed to a sliding marker, prevents air spaces from altering the density of the film. Further, placing the plurality of rotating markers at precise predefined offsets assures that the markers are always within the beam and thus imageable. Each rotating wheel 305 also includes a small black dot 306 positioned at a 90 degree offset to the rotating disk marker 304. The black dot 306 is used to determine the light field edges on the sampled image. For each of the four sides of the light beam projection of the LINAC light localizer on the surface of the imaging phantom, the wheels 305 on that edge are rotated such that the black dots 306 are positioned at the light field edge. Although the light field edges are not viewable in the sampled image, the rotating disk markers 304 are viewable. From the sampled image, using the observed positions of the disk marker 304 and the geometric relationship (i.e., 90 degrees) between the disk markers 304 and the black dot 306, the light field edge in the sampled image is determined.

Once the disk markers 304 are manually adjusted to the light field edges, the imaging phantom 10 is then exposed to a beam of radiation for a dose of 20–50 cGy, irrespective of the beam energy. It is noted, however, that the preferred embodiment of the imaging phantom 10 was designed for a minimum photon beam energy of 6 MeV.

FIG. 4 is an illustration of a sheet of Kodak XV-2™ film showing the recorded radiation field including the images of the fixed and rotatable markers of the imaging phantom 10. Subsequent to recording a sample of the photon beam on radiographic film, the exposed film is digitized using a 12 or 16 bit digitizer 60 having a resolution of 50 dpi or greater. It is noted that lower resolutions may be used at the expense of lower overall accuracy. Suitable electrical connections are made to pass the output signal from the digitizer to the computer 20 where it is stored as an image file in the computer database 40 for eventual processing by image analysis software.

The processing of the sampled image covers a significant aspect of the invention. The present invention provides software to perform image quality assessment. Once an image file of a sampled beam image is acquired and stored in the database 40, it can then be recalled and processed in accordance with the present invention. Processing the sampled image includes two major aspects. In a first aspect, software routines are employed that pertain to the detection and registration of objects within the sampled image. Registration of the sampled image provides all the information necessary prior to calculating the set of beam quality assurance parameters. In a second aspect, software routines are employed that pertain to the extraction and analysis of information from the phantom image to calculate the light field edge of the LINAC radiation machine light field localizer is found in the sampled image. The light field edge marks are determined by a set of objective beam quality assurance parameters.

B.2 Detection and Registration

Before a sampled beam image can be analyzed by the image analysis system the location of the images of the fixed disk markers 202a–h and the rotatable disk markers 205a–h on the sampled image are determined. This is achieved by analysis software included in the image analysis system. Detection and registration of the markers 202a–h within the sampled image establish an x-y reference coordinate system, and determine the actual rotation, position and magnification of the imaging phantom 10 with respect to the radiographic film packet.

The analysis software uses information about the computed radiation field size to approximate the position of the fixed disk markers. The computed radiation field size may be determined by assuming that the center of the radiation field will be very close to the center of the imaging phantom 10. One exception is where the imaging phantom 10 is incorrectly set up in the beam's radiation field. Otherwise, knowing a-priori the position of the fixed markers relative to the center of the imaging phantom 10 in the actual imaging phantom 10, the fixed disk markers 202a–h are then searched for in the sampled image in the general vicinity of their actual locations on the imaging phantom using a marker detection algorithm. The analysis software uses the information gained from markers 202a–h that have been detected to assist in locating markers not yet detected.

The position of the fixed markers 202a–h in the sampled image provides full knowledge of the IBQA phantom orientation (i.e., the center of the IBQA phantom, the rotation of the IBQA phantom and the magnification of the image of the IBQA phantom on the recording film, where the magnification refers to the relationship between the number of pixels in the image which represent 1 cm). The position of the fixed markers 202a–h also provide information related to the orientation and size on the image and the centers and edges of the rotatable disks.

Upon determining the position of the fixed markers 202a–h in the sampled image, the positions of the rotatable markers are searched for to determine the edges of the light field. The location of the light field edge requires knowledge of the positions of both the fixed and the rotatable (disk) markers. The position of the mark, which determines the light field edge, can only be determined by knowing the position of the rotatable markers and the centers of the rotatable disks, which in turn can only be determined by knowing the overall position of the IBQA phantom from the position of the fixed markers whose positions are determined as discussed above. What remains therefore is a means for determining the positions of the rotatable (disk) markers. As discussed above, for each of the four sides of the light beam projection of the LINAC light localizer on the surface of the imaging phantom, a rotatable disk on that edge is rotated such that the black dot on the rotatable disk is positioned at the light field edge. Although the light field edges are not viewable in the sampled image, the rotating disk markers are viewable. From the sampled image, using the observed positions of the rotatable (disk) marker and the geometric relationship (i.e., 90 degrees) between the disk markers and the black dot on the rotatable disk, the light field edge can be determined in the sampled image.

The positions of the rotatable markers which are housed in the rotatable disks are then searched at a radius from the centers of the rotatable disks. The light field edge markers are positioned at the same radius as the markers located above from the disk center but oriented ninety degrees from the markers. The two light field marks along each edge determines the light field edges.

B.3 Parameter Extraction

Upon completion of performing detection and registration, the beam quality assurance parameters are calculated. The present invention includes software as part of the IIA system to calculate the beam quality assurance parameters to monitor image quality. The use of an automated system to measure image quality allows for a far greater accuracy in measuring system performance above and beyond traditional visual or interactive diagnostic procedures. A measurable level of image quality is obtained through the use of a set of consistent image parameters automatically computed with minimal operator assistance. The result of this software system is a completely objective, repeatable process that can be invoked by the users of this system much more rapidly than can be achieved by traditional visual or interactive diagnostic procedures.

The software in the preferred embodiment of the present invention is developed in Visual Basic and is intended for operation using a WINDOWS™ based operating system, such as Windows 9x OS™ or Windows NT 4.0+ OS™. The software was written as a collection of individual modules. It is contemplated that the modular construction enables incorporation of future imaging phantoms and analysis routines.

B.3.1 Software Hierarchy

Figure 5:
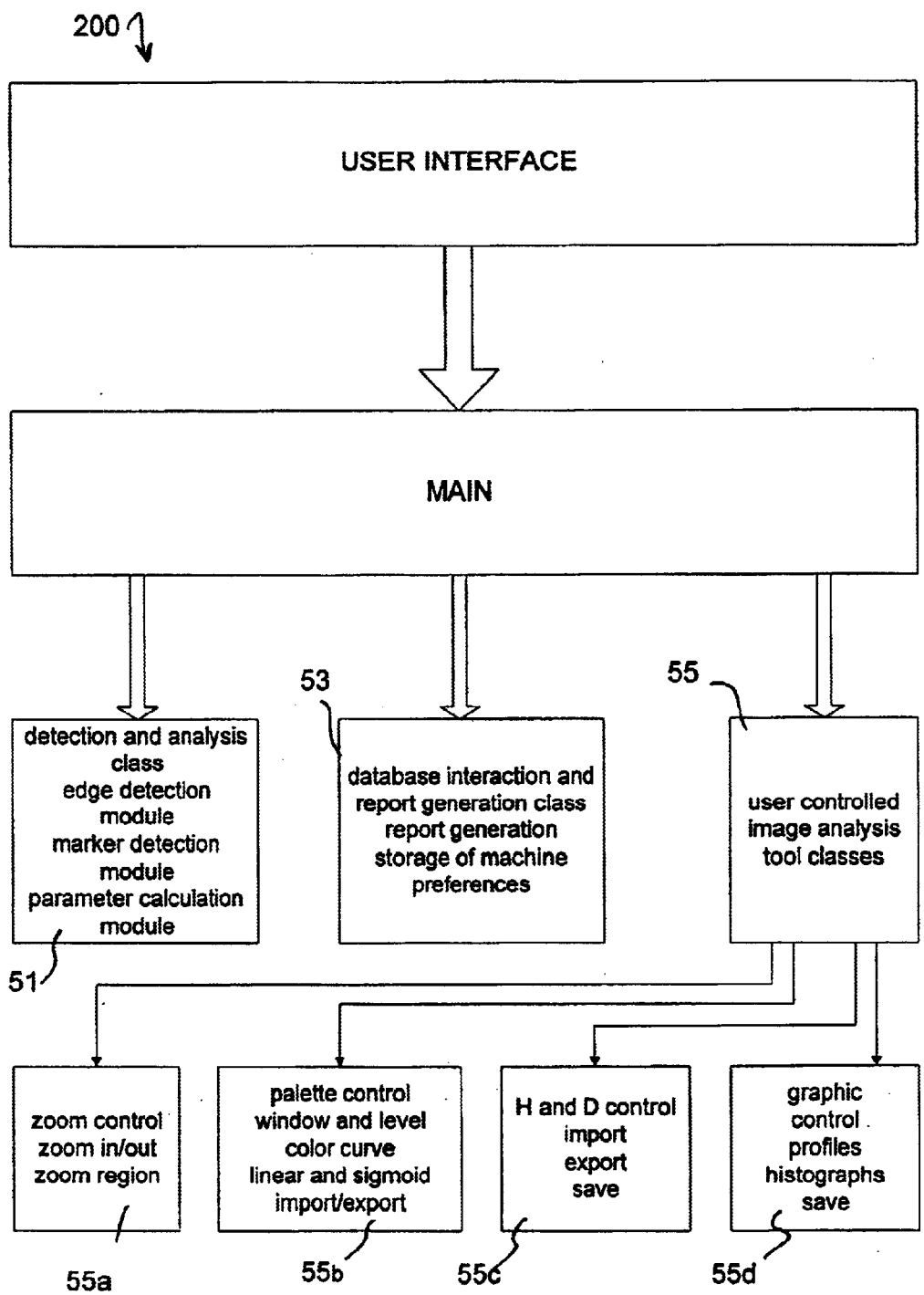
FIG. 5 is a block diagram of the software structure of the image-based quality assurance system (IBQA) according to the present invention.

FIG. 5 is a block diagram of the software structure of the IIA system 200. FIG. 5 shows the IIA software organized into three general classes, a detection and analysis class 51, a database interaction and report generation class, 53, and a user controlled image analysis tool class 55. Each class includes one or more constituent software modules. The modular structure illustrated in FIG. 5 permits individual software modules to be easily replaced or modified.

The detection and analysis class 51 includes an edge detection software module, a marker detection module, an image correction software module, and a parameter calculation module. The detection and analysis class 51 modules require as input: the image file, values for smoothing and line thickness masks which are used for filtering out noise, and a protocol parameter which determines the equations used to calculate some of the the image quality assurance parameters, such as flatness.

The edge detection module detects the radiation field edge of the sampled image. The detection module assumes that the edges lie within a fraction of the dimension of the file near the field edge. The field edges are detected by fitting a polynomial to the pixel value around the threshold value in several positions along each edge. The rough position of the rod edge is found by simply searching in from the field edge until the threshold is crossed, without recrossing the threshold.

Subsequent to performing edge detection, the marker detection module is instantiated to detect the images of the fixed 202*a–h* and rotatable 205*a–h* radio-opaque markers in the sampled image. The marker detection module relies on detection and localization routines which utilize the a-priori knowledge of the actual marker positions in the imaging phantom, and the assumption that shifts and rotations of the radiation field and the imaging phantom are less than 2 cm and less than 30°, respectively. Given the assumptions and after determining the radiation field localization, the approximate marker positions are known. As such, only regions around the suspected marker regions (i.e, regions of interest (ROI)) need to be searched by the marker detection module.

The marker positions within a ROI are determined by two separate detection routines. The first detection routine uses a method comparable to that described in Luchka, K; Shalev, S.; et al., "Assessing radiation and light field congruence with a video based electronic portal imaging device." Med. Phy. 23, 7 1996, pgs. 1245–1252. The first detection routine uses a mask that approximates a circle to discriminate pixels. The exact size of the mask is dependent on the pixel per cm (PPCM) of the image as approximated using the radiation field size. The mask selects pixels such that the pixel values on the edge of the circle are diameter greater than or less than the center pixel by an amount greater than the average noise at the center of the radiation field, where the inequality is dependent on the image intensity slope (IIS) which is determined by the radiation field intensity relative to the background intensity.

Pixels that satisfy this mask are grouped together if they are adjacent to one another. A group of pixels are collectively considered to identify a radio-opaque marker if they have more than a predetermined number of connected pixels. If any of the pixels that make up a group lie along the edge of the region of interest, then the region of interest is expanded along that edge by the assumed diameter of the marker and the search continues in the expanded region. Once all pixels that make up a marker have been found, the center of the marker is determined as the centroid of those pixels.

The second detection method uses the same mask as described above, however, the selected pixels are further discriminated by sampling pixels along three successively larger circles centered at that pixel. Specifically, with diameters of 0.25 cm, 0.5 cm, and 0.75 cm, referred to as circle 1, 2 and 3, respectively. The average pixel value along larger circles must be greater than or less than the average pixel values along the smaller circles as well as the center pixel value. All pixels that satisfy this criterion and that lie within a region of size three times the marker radius is considered from the same marker and are used to determine the marker center, determined as the centroid.

Both the first and second detection methods locate markers within a region of interest and determine the marker's center within a set number of pixels before a marker position is accepted.

Once all marker positions have been determined, the imaging phantom coordinate system is known exactly, and thus the center of the imaging phantom 10 as well as the centers of the rotatable disks 204*a–h* are known.

At this point, the light field edge of the LINAC light field localizer is found in the sampled image. The light field edge marks are determined by calculating the position of the rotatable disk markers 204*a–h* in the image and using the geometric relationship which positions the light field edge 90 degrees from the disk marker position.

At this point the image correction module is invoked to correct for artifacts introduced into the image by the digitizer, developer or other sources. The three main artifacts are background pixel variation across the image, pixel width variation across the image and stray marks on the film.

The image processing module uses smoothing and averaging techniques, as known in the art, to resolve stray marks and noise on the sampled image. The pixel width variation across a sampled image results in a spatial non-linearity where the physical distance represented by a number of pixels is different depending on the positions of those pixels on the sampled image. For example, a number of pixels on the right side of the image file may represent a distance of x cm, while on the left side of the sampled image the same number of pixels may represent a distance of x+k cm. The image processing software modules attempts to correct for this variation by using the known radiographic marker positions to determine the spatial distance variation across the digitized film. The distance between adjacent fixed markers gives a measure of the average cm/pixel in that region. The cm/pixel value of adjacent regions are fit to a linear function with the independent variable being the pixel position, thus giving an estimate of the varying width of a pixel across the file. The image is corrected by normalizing the width of each pixel across the file. At this point the image quality assurance parameters are calculated by instantiating the parameter calculation module. The image quality assurance parameters to be measured include: the radiation field size, the radiation field edge rotation, the radiation light field edge, the LINAC crosshair center shift, the light field size, the light field center shift, penumbra, radiation flatness, and radiation symmetry.

The center of the radiation field is the centroid of the four corner points which are defined from the intersection of the edge lines. The radiation field size is calculated as a distance between two points on opposite edges of the radiation field. These two points are defined as the intersection points between a line parallel to the radiation field axis passing through the radiation field center and the lines that define the edge of the radiation field. The distance is then corrected to represent its value at the surface of the phantom.

The radiation field edge rotation is computed as the angle between the radiation field edge and the angles of the phantom axis.

The radiation light field edge coincidence is computed as the distance between the radiation field edge and light field edge. It is calculated for each edge as the distance between 2 points defined by the intersection between the edge lines (both radiation field edge and light field edge) and the radiation field axis line passing through the radiation field center. The radiation edge positions are corrected to line in the surface plane before the distance is calculated.

The LINAC crosshair center shift is computed as the distance between the radiation field center and the center of the phantom, which is set up to the crosshairs. This distance is corrected to the surface of the phantom.

The light field center is found using the same method described above for the radiation field. In particular, the light field size is computed as the distance between two points from opposite edges of the light field. These two points are defined as the intersection points between a line parallel to the light field axis passing through the light field center and the lines that define the edge of the light field. The light field center shift is the distance between the center of the radiation field and the center of the light field.

The following parameters are measured from a profile array extracted from the image file. The profile array holds the pixel values associated with a line passing through the radiation field center along the radiation field axis and extending approximately 2 cm pass the 50% pixel value on the edge of the radiation field. The profile arrays are sampled starting from the center of the radiation field and extend out in both directions along the radiation field axis discussed above. Since the radiation field axis does not necessarily coincide with the film axis the values within the array maybe interpolated between the four nearest pixels spaced one pixel distance apart. Depending on the user's preferences the actual values in the array may be an average of pixel values (again interpolated values) perpendicular to the array line and/or are values resulting from smoothing the original array values. The following parameters are calculated from values from these arrays.

The penumbra is a measure of the width of the radiation field edge. It is the measure of the physical distance between the pixel values that are 80% and 20% of the radiation field center. These values are found by searching the profile arrays near the 50% radiation field edge position for the threshold position representing the 80% and 20% values. The pixel around the threshold are fit to a second degree polynomial and the positions of the 80% and 20% values along the fit equations are recorded.

Radiation flatness is the measure of the variation of the photon beam from its maximum value to its minimum value along each profile. Radiaton symmetry is a measure of the variations beam from one side to a symmetric point on the opposite side of the radiation field center. These values are determined by various combination of max, min, average and other number extracted from the radiation profiles. The exact equations are dependent on the protocol used, but are similar for each protocol. At present the IBQA supports three protocols. The equations used for each protocol are shown below.

The IBQA software routines extract all parameters required for both flatness and symmetry for any protocol, regardless of the protocol specified. All parameters values have the film background subtracted from them. The central axis value is the average of a region around the radiation field center. The parameters extraction starts at the center of the radiation field center (the zero element of the array). The array is searched moving out from the center alternating from one side of the radiation field center to the other. The search continues until the edge of the prescribed region is searched. The maximum, minimum and average values are recorded. Upon alternating from one side of the radiation field center, the difference between the 2 points that are the same distance from the center is sampled. The maximum difference of all symmetric points and the average symmetric difference are recorded. These values are used to calculate the flatness and symmetry value using the formulas describe below.

The values for flatness and symmetry are calculated under the first protocol as follows:

Flatness=$([A/(A+(CA)/2]-1)*100$

Where A is the maximum value along a profile line or minimum value depending on which has the greater difference with Central Axis (CA) value.

Symmetry=$[(A/B)-1]*100$

Where A is the value of the larger of the two symmetric points on profile, where the points represent the greatest difference between each other as compared to other symmetric points. Where B is the smaller of the two points described above.

The values for flatness and symmetry calculated under the second protocol are as follows:

Flatness=$[(A-B)/((A+B)/2)]*100$

Where A is the maximum value along a profile and B is the minimum value along a profile.

Symmetry=$(A-B)/(A+B)/2))$

Where A and B are as described above for the first protocol for symmetry.

The values for flatness and symmetry calculated under the third protocol are as follows:

Flatness=$(A/(CA))*100$

Where A is the value that represents the largest difference from the central axis value. The symmetry value is identical to that shown for the second protocol.

Symmetry=$(A-B)/((A+B)/2))$

C. Image Analysis

The present invention also includes additional analysis software 55, as shown in FIG. 5, to allow an operator to manually analyze the digitized image. The analysis software includes a number of software utilities for modifying automatically measured results and for analyzing a sampled image. The software utilities are described as elements 55a–d in FIG. 5.

After image registration an operator can inspect and adjust the position of the detected markers before any other image analysis is performed. The image is then analyzed using the new marker positions.

Another utility provided by the analysis software 55 is a H&D (i.e., Hunter and Driffield) mapping control that allows an operator to define an H&D curve to convert an intensity image to a dose map prior to analyzing the sampled image.

Another utility provided by the analysis software 55 is graphing control 55d which includes an interactive profiler that displays the pixel value intensities along a user defined line as well as the lines that pass through the line, and has optional smoothing and line thickness averaging. The graphing control utility 55d also can display the historgram of the image or within a region of interest (ROI).

Figure 8:
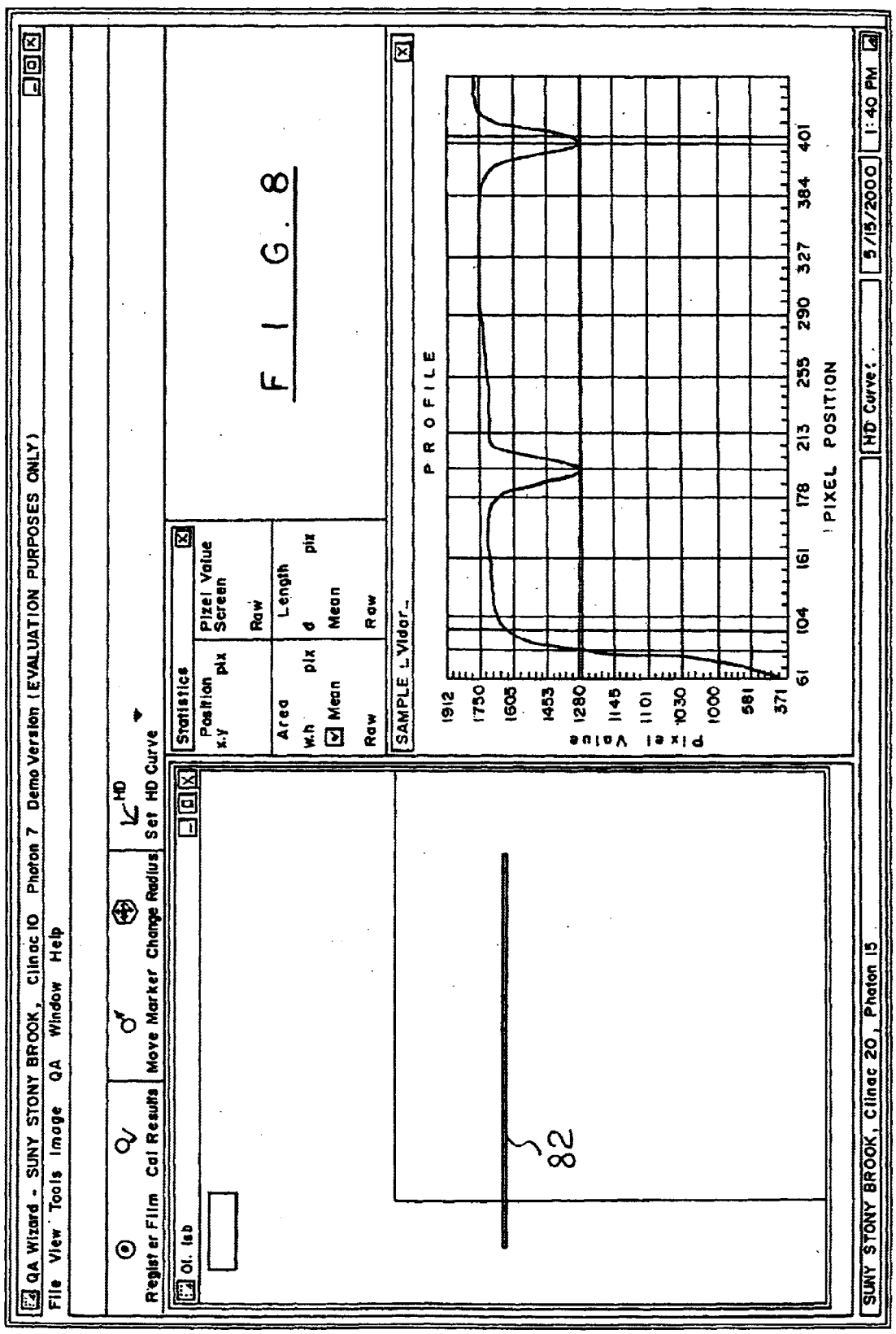
FIG. 8 is a screen shot of a display of the image profile software which is a component of an integrated image analysis (IIA) system according to the present invention.

FIG. 8 is an illustration of an image file on the left hand side, and a pixel profile of line 82 on the image. Line 82 passes through the edge of the radiation field and through one of the markers. The profile tool shows, in addition to pixel intensity profile, the positions of the detected radiation and light field edges and the centers of the markers for markers that line 82 passes through. This feature is helpful in verifying the accuracy of the detection routine. The detected marker centers' will lay at the very bottom of the marker profile if the center is positioned correctly.

The database 40 stores the plurality of image quality assurance parameters for each operator session. Parameter changes are tracked over time to provide a quantitative measure of changes with time. Table I illustrates the tracking of changes in the mechanical QA parameters.

D. Report Generation

The database interaction and report generation class 53 of FIG. 5 includes a report generation module and a machine preferences module.

Referring first to the machine preferences module, during initial program configuration the operator registers all radiation machines for which they are responsible. The database 40 stores user preferences for each machine specified. The preferences include the smoothing mask sizes and line averaging sizes which are used in analysis modules, as well as the protocol, baselines and tolerance values for the measured parameters for each energy. The baseline and tolerance values are used for comparison with analysis results. In addition, the database 40 stores the analysis results. Each time a result is stored in the database 40, tolerance for that energy as well as the analysis date, associated energy, machine, and institution are included to maintain a complete record of that result.

Referring now to the report generation module, when an analysis is completed the results are presented on screen. If measured image quality assurance parameters fall outside the baseline performance limits the parameter will be displayed in bold in a printed (i.e., hardcopy) report, as shown in FIG. 7.

While the invention is susceptible to various modifications and alternative forms, specific embodiments thereof have been shown by way of example in the drawings and have been described in detail. It should be understood, however, that it is not intended to limit the invention to the particular forms disclosed, but on the contrary, the intention is to cover all modifications, equivalents and alternatives falling within the spirit and scope of the invention as defined by the appended claims.

What is claimed is:

1. A quality assurance device for measuring at least one beam quality assurance parameter of a beam emitted from a linear accelerator (LINAC), the device comprising:

a housing having a top surface and a bottom surface and configured for placement in the direction of the emitted beam; and a plurality of fixed and movable markers disposed on said top surface for measuring said at least one beam quality parameter, each of said plurality of movable markers being located within respective rotating wheels located on said top surface for determining a degree of misalignment between a LINAC's beam field edges and a LINAC localizing light field.

2. The quality assurance device of claim 1, wherein said housing includes a chamber configured to receive a radiographic film for obtaining a sampled image of said emitted beam.

3. The quality assurance device of claim 1, wherein said markers are radio-opaque.

4. The quality assurance device of claim 1, wherein said markers are constructed of a material selected from the group comprising tungsten, steel, titanium, lead or other denser material.

5. The quality assurance device of claim 1, wherein said fixed markers are positioned linearly along each of two orthogonal axes of said top surface.

6. The quality assurance device of claim 1, wherein said housing is constructed of a polystyrene composite.

7. The quality assurance device of claim 1, wherein said at least one beam quality assurance parameter is selected from the group consisting of radiation beam symmetry, radiation beam uniformity, radiation field size, coincidence between a LINAC light beam localizer and a radiation field, accuracy of beam cross-hair placement, constancy of radiation field penumbra, and collimator jaw angle and alignment.

8. The quality assurance device of claim 1, further comprising two scribed orthogonal lines intersecting at a central position of the top surface for centering the emitted beam with a localizing light emitted from said LINAC.

9. An image quality assurance system for assessing image quality of a beam emitted from a linear accelerator(LINAC) by measuring at least one beam quality assurance parameter, said system comprising:

means for acquiring a sampled image of the LINAC beam; and means for measuring and analyzing said at least one beam quality assurance parameter using the sampled image, said measuring means including software means for:

detecting at least one radiation field edge of the sampled image;

detecting images of the plurality of fixed and rotatable radio-opaque markers;

determining the light field edge of the LINAC radiation machine light field localizer in the sampled image; and determining said at least one beam quality assurance parameter for monitoring image quality.

10. The image quality assurance system of claim 9, wherein said acquiring means includes a quality assurance device having a plurality of fixed and rotatable markers disposed on a top surface of a top plate, said quality assurance device further including a bottom plate, and an inner chamber configured for receiving film.

11. The image quality assurance system of claim 10, wherein said means for measuring and analyzing includes:

means for recalculating the positions of rotatable markers and light fields in the sampled image;

means for correcting for non-linearities in the image;

means for retrieving profile arrays; and means for finding positions of penumbras.

12. The image quality assurance system of claim 9, wherein said sampled image includes images of said plurality of fixed and rotatable markers for establishing an x-y coordinate system.

13. The automated image quality assurance system of claim 9, further comprising storing means for storing:

preferred baseline values for multiple beam energies and modalities for different LINACS; and said at least one quality assurance parameter to monitor value differences over time and for generating reports.

14. A method for measuring at least one beam quality assurance parameter of a beam emitted from a linear accelerator (LINAC) using a quality assurance device having a housing including a top surface and a bottom surface and a plurality of markers disposed on said top surface for measuring said at least one beam quality parameter, the method comprising the steps of:

(a) positioning the quality assurance device in a plane substantially aligned with the emitted beam;
(b) inserting a sheet of film into a chamber of the housing;
(c) aligning cross-hairs of the quality assurance device with LINAC localizer cross hairs;
(d) adjusting the LINAC beam field size; and
(f) adjusting the plurality of markers to substantially align with respective edges of a projection of the LINAC's localizer light beam, said localizer light beam being projected onto the top surface of said quality assurance device.

15. A method for measuring at least one beam quality assurance parameter of a beam emitted from a linear accelerator (LINAC) using a quality assurance device having a housing including a top surface and a bottom surface and a plurality of markers disposed on the top surface for measuring the at least one beam quality parameter, wherein the method comprising the step of:

adjusting the plurality of markers to substantially align with respective edges of a projection of the LINAC's localizer light beam, the localizer light beam being projected onto the top surface of the quality assurance device.

* * * * *